United States Patent [19]

Naparstek

[11] Patent Number: 5,789,260
[45] Date of Patent: Aug. 4, 1998

[54] LUPUS DISEASE IMMUNOASSAY METHODS

[75] Inventor: Yaakov Naparstek, Jerusalem, Israel

[73] Assignee: Hadasit Medical Research Services & Development Co., Ltd., Jerusalem, Israel

[21] Appl. No.: 715,097

[22] Filed: Sep. 17, 1996

Related U.S. Application Data

[63] Continuation of Ser. No. 395,697, Feb. 28, 1995, abandoned.

[30] Foreign Application Priority Data

Mar. 1, 1994 [IL] Israel ........................ 108811

[51] Int. Cl.$^6$ .................. G01N 33/564; G01N 33/543
[52] U.S. Cl. .................. 436/506; 436/518; 436/811; 435/7.92
[58] Field of Search ................ 435/7.1, 7.9, 7.92, 435/7.94; 436/506, 518, 811; 530/353, 403, 834

[56] References Cited

U.S. PATENT DOCUMENTS 5,340,720  8/1994  Stetler ........................ 435/7.4

OTHER PUBLICATIONS

Clin. Exp. Immunol. (1994), 96(1), 26–30 Coden: Cexial; ISSN: 0009–9104, 1994 M.S. Atta et al., "The Influence of anti–fibronectin antibodies on interactions involving extracellular matrix components and cells: A possible pathogenic mechanism".

Clin. Exp. Immunol. 91 (3), 1993, 442–448, Coden: Cexial ISSN: 0009–9104, R.A. Treurniet et al., "Gender–Related Influences on the Development of Chronic Graft–Versus–Host Disease–Induced Experimental Lupus Nephritis".

Yokohama Medical Bulletin, vol. 43, No. 1–2, Feb. 1992, pp. 7–15, Tetsuo Sasaki et al., "Immunohistochemical Assessment of Basement Membrane Composing Proteins in Bullous and Collagen Diseases".

The Journal of Immunology, vol. 151, No. 2, Jul. 15, 1993, Baltimore, US, pp. 814–824, Mary H. Foster et al., "Molecular Analysis of Spontaneous Nephrotrophic Anti–Laminin Antibodies in an Autoimmune MRL–Ipr Mouse".

The Journal of Rheumatology, vol. 10, No. 6, Dec. 1983, Toronto, CA, pp. 913–919, Nancy L. Meryhew et al., "Urinary Excretion of Antinuclear Antibodies".

Foster et al., "Molecular Analysis of Spontaneous Nephrotrophic Anti–Laminin Antibodies in an Autoimmune MRL–Ipr/Ipr Mouse", J. Immunology 151, 814–824, 1993.

Kaplan et al., "Clinical Chemistry", C. V. Mosby Co., St. Louis, pp. 1004–1005, 1984.

Termaat et al., Antigen Specificity of Antibodies Bound to Glomeruli of Mice with Systemic Lupus Erythematosus–like syndromes, Lab. Invest. 68, 164–173 (1993).

Liotta et al., Biochemical Interactions of Tumor Cells with Basement Membranes, Ann. Rev. Biochem. 55, 1037–1057 (1986).

Ten et al., The 1982 Revised Criteria for the Classification of Systemic Lupus Erythematosus, Arth. Rheum. 25, 1271–1277 (1982).

Timpl, Recent Advances in the Biochemistry of Glomerular Basement Membrane, Kidney International 30, 293–298 (1986).

*Primary Examiner*—Marian C. Knode
*Assistant Examiner*—Donna C. Wortman
*Attorney, Agent, or Firm*—Sughrue, Mion, Zinn, Macpeak & Seas, PLLC

[57] ABSTRACT

The invention provides an immunoassay reagent for the binding and detection of antibodies found in the urine of lupus disease patients, comprising extracellular matrix.

9 Claims, 5 Drawing Sheets

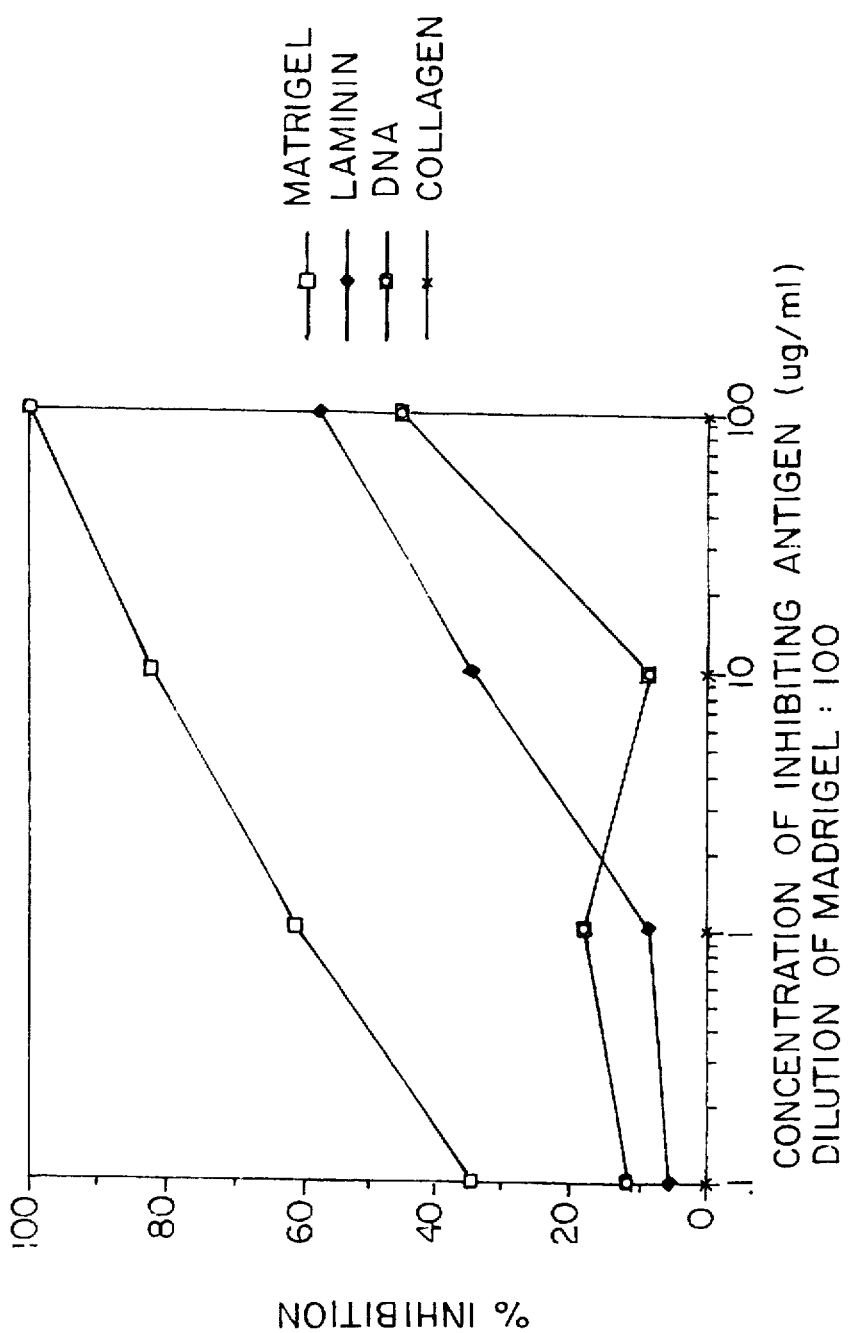

LUPUS DISEASE IMMUNOASSAY METHODS

This is continuation of application Ser. No. 08/395,697 filed Feb. 28, 1995, now abandoned.

The present invention relates to immunoassay reagents, kits and methods.

More particularly, the present invention relates to a novel reagent for binding and detection of antibodies found in the urine of lupus disease patients, and to kits and methods incorporating the same.

Systemic lupus erythematosus (SLE) is a disease of unknown etiology, in which tissues and cells are damaged by deposition of pathogenic autoantibodies and immune complexes. Ninety percent of cases are in women, usually of childbearing age, but children, men, and the elderly can be affected. In the United States, the prevalence of SLE in urban areas varies from 15 to 50 per 100,000; it is more common and more severe in blacks than in whites. Hispanic and Asian populations are also susceptible.

Production of pathogenic antibodies and immune complexes, coupled with failure to suppress them, are the basic abnormalities underlying SLE. Known antibodies associated with SLE are listed below. Not all antibodies or immune complexes are pathogenic; some antibodies cause disease because of their antigen specificity. Examples of these are antibodies to erythrocyte surface antigens, or to coagulation factors. Other antibodies cause disease because of their immunoglobin (Ig) isotype, ability to fix complement (C'), avidity, and/or electrical charge. For example, complement-fixing, cationic antibodies bind to the polyanions in glomerular basement membrane, bind antigen, and cause damage.

The pathogenesis of SLE includes genetic, environmental, and sex hormonal factors. These result in abnormal humoral and cellular immune responses and inadequate clearing of antibodies and immune complexes.

Previously-known autoantibodies in patients with SLE were antinuclear antibodies; anti-DNA; anti-Sm; anti-RNP; anti-RO (SSA); anti-La (SSB); antihistone; anticardiolipin; antierythrocyte; antiplatelet; antilymphocyte; antineuronal.

Antibody binding assay methods have been used to detect the presence of SLE. As is known, specific antibody binding assay methods, also called immunoassay methods, are a rapidly emerging analytical technique, most widely used in diagnosis and research, owing to their high specificity and sensitivity. The earlier versions of this technique, which used radioisotopic labels, have in recent years been increasingly replaced by enzyme immunoassay (EIA) techniques using enzyme labels, which techniques are equally sensitive but safer, simpler, and cheaper.

Among the EIA techniques, the so-called "heterogenous" assay methods are commonly used, employing enzyme-labelled antibodies or antigens attached to sensitized surfaces of solid carriers, such as test tubes, polystyrene beads, or plates provided with recessed wells. Such techniques are generally referred to by the abbreviation ELISA, which stands for "enzyme-linked immunosorbent assay." In accordance with one modification, this technique is combined with the known use of a second antibody, namely, an antiserum to the specific first antibody. The second antibody serves as non-specific detector for any first antibody, either in the free state or when bound to its specific antigen in an antigen-antibody complex.

In accordance with one version of the above method, which reacts also to the known coated tube technique, an antigen is attached to the inner wall surface of a test tube in which the binding reaction is then carried out, whereupon the free specific antibody to said antigen present in the test sample will be attached to the surface of the tube via the antigen immobilized thereon. Thereafter, the liquid reaction mixture is removed from the test tube, the latter is washed, and a second solution containing an enzyme-labelled second antibody is introduced into the tube. This labelled second antibody will also be immobilized by attaching itself to any antibody which is bound to the surface of the tube via the antigen. The test tube is again emptied, rinsed, and filled with a suitable substrate responsive to the enzyme label of the second antibody, and the enzymatic activity is measured. This activity is directly proportional to the antibody concentration in the test sample.

As stated above, systemic lupus erythematosus is characterized by the occurrence of a variety of autoantibodies. Many of these antibodies bind to intracellular antigens (i.e., nuclear antigens) in vitro; however, their in vivo ligand is not defined.

Thus, as reported in *Harrison's Principles of Internal Medicine*, 12th Ed., McGraw-Hill, New York, U.S.A., p. 1435 (1991):

"The presence of characteristic antibodies confirms the diagnosis of SLE. Anti-nuclear antibodies are the best screening test. If the test substrate is living human nuclei, as in WIL-2 or HEP-2 cells, more than 95 percent of lupus patients will have positive tests. Rodent liver or kidney substrates do not detect as wide a range of ANA or anticytoplasmic antibodies; approximately 85 percent of SLE serums are positive on those substrates. A positive ANA is not specific for SLE; ANA occurs (usually in low titer) in some normal individuals; the frequency increases with aging. Furthermore, other autoimmune disease, acute viral infections, chronic inflammatory processes, and several drugs may cause ANA positively. Therefore, a positive ANA supports a diagnosis of SLE but is not specific; a negative ANA makes the diagnosis unlikely but not impossible. Antibodies to dsDNA and to Sm are relatively specific for SLE; other autoantibodies listed above are not. High serum levels of ANA and anti-DNA and low levels of complement usually reflect disease activity, especially in patients with nephritis. Serum levels of cryoglobulins or other immune complexes occasionally correlate with disease activity. Total functional meolytic complement ($CH_{50}$) levels are the most sensitive measure of complement activation, but are also most subject to laboratory error. Quantitative levels of C3 and C4 are widely available. Very low levels of $CH_{50}$ with normal levels of C3 suggest inherited deficiency of a complement component."

Thus, while certain characterizing antibodies of SLE have been identified and are even used for diagnostic purposes, these antibodies do not have an identified in vivo ligand, and even the best screening test using ANA is not considered to be specific.

Furthermore, the presence and/or titer of said antibodies heretofore do not reflect disease activity in the kidney, which is of special importance.

According to the present invention, there has now been found a novel group of autoantibodies that seems to play a role in lupus nephritis. These antibodies have the following characteristics:

a) they bind to extracellular matrix (ECM) components;

b) they occur specifically in the urine of SLE patients;

c) their level correlates with the activity of renal disease.

Furthermore, it has now been found that the urine of lupus patients with active disease contains antibodies that bind to ECM produced by endothelial cells, as well as to the ECM produced by epithelial cells (MATRIGEL®). It binds to the 200 kDa chain of laminin, as well as to two unknown proteins in MATRIGEL® having, respectively, a molecular weight of about 97 and about 116 kDa.

Based on these discoveries, according to the present invention there is now provided an immunoassay reagent for the binding and detection of antibodies found in the urine of lupus disease patients, comprising extracellular matrix.

For use in the present invention, said extracellular matrix is derived from endothelial cells or from epithelial cells.

The invention also provides an immunoassay reagent for the binding and detection of antibodies found in the urine of lupus disease patients, comprising laminin. Especially preferred for use in the present invention is laminin having a molecular weight of about 200 kDa.

In another aspect of the present invention, there is provided a test kit for immunoassay detection of antibodies found in the urine of lupus disease patients, comprising one or more containers having extracellular matrix or a lupus antibody-binding laminin component thereof attached to their inner surfaces.

The invention further provides a binding assay method for determining the presence of antibodies found in the urine of lupus disease patients, comprising the steps of:

a) incubating a suspected urine sample in contact with a solid carrier having extracellular matrix or a lupus antibody-binding laminin component thereof fixed on at least a portion of its surface;

b) washing said carrier to remove residual samples;

c) incubating the solid carrier with anti-human/mouse IgG peroxidase or alkaline phosphatase conjugates;

d) incubating said solid carrier in contact with a suitable enzyme substrate which undergoes color change in the presence of bound conjugate; and e) measuring the intensity of resultant color.

As will be realized, the method of the present invention can be used for monitoring the progression of lupus disease, as well as for predicting an active phase of lupus in a patient with a disposition to said disease.

Thus, according to the present invention, there is also provided a binding assay method for determining the progression of lupus disease in a patient, comprising the steps of:

a) incubating a suspected urine sample in contact with a solid carrier having extracellular matrix or a lupus antibody-binding laminin component thereof fixed on at least a portion of its surface;

b) washing said carrier to remove residual samples;

c) incubating the solid carrier with anti-human/mouse IgG peroxidase or alkaline phosphatase conjugates;

d) incubating said solid carrier in contact with a suitable enzyme substrate which undergoes color change in the presence of bound conjugate;

e) measuring the intensity of resultant color; and f) repeating steps (a) to (e) with fresh urine samples obtained from said patient, after a predetermined number of days.

Said predetermined number of days can be measured in days, weeks, or months, depending on the doctor's recommendation.

The invention also provides a binding assay method for predicting an active phase of lupus disease in a patient with disposition to said disease, comprising the steps of:

a) incubating a suspected urine sample in contact with a solid carrier having extracellular matrix or a lupus antibody-binding laminin component thereof fixed on at least a portion of its surface;

b) washing said carrier to remove residual samples;

c) incubating the solid carrier with anti-human/mouse IgG peroxidase or alkaline phosphatase conjugates;

d) incubating said solid carrier in contact with a suitable enzyme substrate which undergoes color change in the presence of bound conjugate; and e) measuring the intensity of resultant color.

In preferred embodiments of the methods of the present invention, said urine is incubated in contact with a solid carrier having laminin fixed on at least a portion of its surface. Preferably, said laminin has a molecular weight of about 200 kDa.

ECM for use in the present invention can be produced by methods known per se, as described, e.g., by Naparstek, et al., Nature, Vol. 310, p. 241 (1984), or commercially purchased. For example, mouse membrane ECM, sold under the tradename Matrigel®, can be obtained from Biological Industries, Ltd., Beit Haemek, Israel, and used in the present invention.

Functionally, the components of ECM serve several roles. They comprise the ECM adhesives which bind cells to one another. They constitute the sheets of acellular basement membrane which, in matrix or scaffold-like fashion, determine the characteristic three-dimensional cellular organization of specific tissues. Other roles of ECM are surprisingly dynamic. ECM components, such as laminin, fibronectin, and the collagens, are attachment factors which mediate the substrate binding and cytoplasmic spreading of anchorage-dependent cells. Some attachment factors, for example laminin, also have intrinsic mitogenic properties, and thus also function as growth factors.

In addition to having attachment and growth properties, specific combinations of ECM components characteristic of given tissues are necessary for the differentiation, or maturation, of epithelioid cells to a state of full morphologic and biochemical function.

Biological Industries, Ltd., in their prospective regarding the Matrigel® product, explain that in vivo ECM is, collectively, all ECM molecules and molecular aggregates which are secreted by cells and which serve as support and framework for three-dimensional tissue organization and function. Specifically, MATRIGEL®, which was used in the examples of the present invention, is described as a multi-component preparation of natural, solubilized tissue basement membrane containing laminin, collagen type IV, heparan sulfate proteoglycan, and entactin (nidogen).

ECM is composed of a number of components, including vimentin, laminin, glycoseamino- glycans, entactin, collagen and fibronectin [R. Timpl, "Recent Advances in the Biochemistry of Glomerular Basement Membrane," Kidney International, Vol. 30, pp. 293–298 (1986)]. The first three components are found in both the endothelial and the epithelial-derived ECM. The C72 monoclonal antibody that reacted with the ECM was found to bind to the laminin component of the ECM. This antibody, derived from NZB/NZW F1 lupus mice, was tested because it represents a major group of lupus antibodies, as it utilizes a VH gene sequence that is common to several murine anti-DNA lupus antibodies. One of the antibodies that uses this VH gene, the A52, has been previously shown to bind to the kidneys and to induce kidney dysfunction in an isolated perfused rat kidney model [E. Raz, et al., "Anti-DNA Antibodies Bind Directly to Renal Antigens and Induce Kidney Dysfunction in the Isolated Perfused Rat Kidney," J. Immunol., Vol. 142, pp. 3076–3082 (1989)]. Recently, the same VH gene has been shown to encode a nephritogenic anti-laminin antibody in the MRL/lpr/lpr model [M. H. Foster, et al., "Molecular Analysis of Spontaneous Nephrotropic Anti-laminin Antibodies in Autoimmune MRL/lpr/lpr Mouse," *J. Immunol.*, Vol. 151, pp. 814–824 (1993)]. The observation that a similar antibody from the NZB/NZW F1 strain of lupus mice also binds to laminin in the ECM, indicates that laminin may indeed be a genuine in vivo renal target antigen for these so-called anti-DNA murine lupus antibodies. The present finding that the binding of the polyclonal murine and human urinary autoantibodies to the ECM was also inhibited by laminin, indicates that laminin is a major target antigen of the nephritogenic human lupus antibodies as well.

The invention will now be described in connection with certain preferred embodiments and examples, with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

In the drawings:

FIGS. 3A and 3B are graphic illustrations of the inhibition of C72 and urine from an SLE patient binding to MATRIGEL®.

Figure 1:
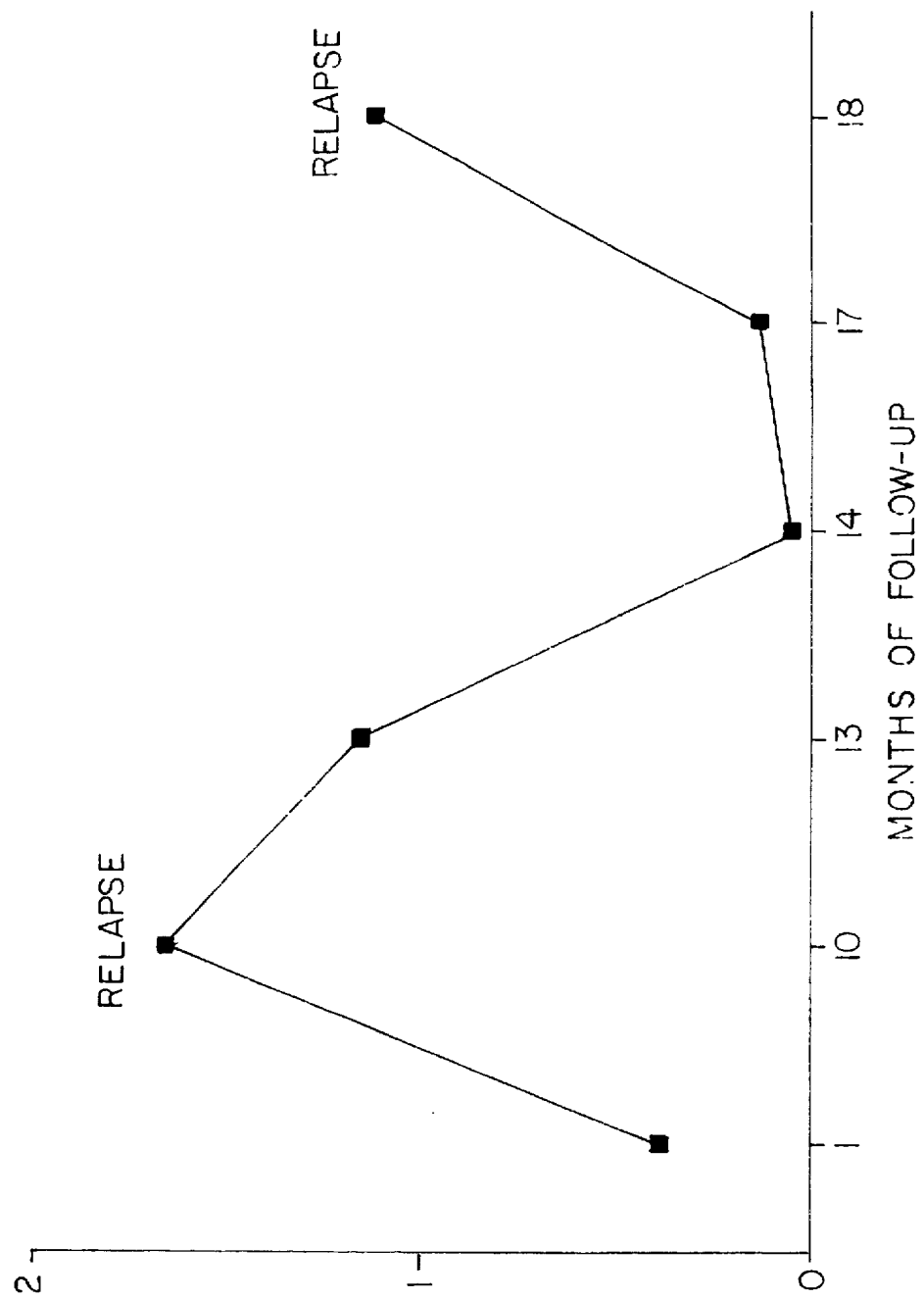
FIG. 1 is a graphic illustration of consecutive measurements of anti-ECM level in a single patient.

EXAMPLE 1
Preparation of Corneal Endothelium ECM Coated Wells

Bovine corneal endothelial cells were grown in Petri dishes, as previously described by Vlodaski, et al., "Degradation of Heparan Sulphate in the Subendothelial Basal Lamina by Normal and Malignant Blood-Borne Cells," in *Extracellular Matrix: Structure and Function*, A. R. Reddi, Ed., Alan R. Liss, Inc., New York, U.S. A., pp. 283–308 (1985). When the cells reached confluence, they were removed by trypsin, washed, counted, and cultured in microwells at a concentration of $10^4$ cell/ml.

Five days after reaching confluence (about ten days after seeding), the cell layer was dissolved by exposure (10 min, 22° C.) to 0.5% Triton X-100 in phosphate buffered saline, leaving the underlying ECM intact and firmly attached to the microwells.

EXAMPLE 2

MATRIGEL® was diluted 1:100, placed in microwells for 30 minutes, and stabilized as in Example 1.

EXAMPLE 3

ECM was bound to microwells and stabilized as in Examples 1 and 2.

To perform the assay, the wells are first incubated with a blocking solution composed of fetal calf serum and bovine serum albumin, to reduce non-specific binding. The wells are washed, and diluted urine or serum samples are placed in the microwells and incubated. If anti-ECM antibodies are present in the samples, they will bind to the antigen in the microwells. After washing the microwells to remove residual sample, a second incubation with anti-human/mouse IgG, conjugated to alkaline phosphatase or to peroxidase, is carried out. Unbound conjugate is removed in the subsequent washing step. Enzyme substrate (p-nitrophenyl phosphate or o-phenylene diamine) is then added, and if bound conjugate is present, the colorless substrate will change its color. The reaction is then stopped and the color fixed. The intensity of the color is measured photometrically at 405 nm (for peroxide), and is proportionate to the concentration of anti-ECM antibodies present in the sample.

Testing the urine and serum of lupus patients, healthy individuals and lupus mice, it was shown that anti-ECM antibodies are found specifically in the urine of lupus patients with active renal disease, and that their level decreases in correlation with the activity of the renal disease.

The results of these tests are set forth and summarized below in Tables 1–3.

TABLE 1

Anti-ECM Antibodies in the Urine of an SLE Patient

| Urine Dilutions | Anti-ECM (O.D.) | |
|---|---|---|
| | SLE Patient | Healthy Control |
| 1:4 | 0.950 | 0.030 |
| 1:100 | 0.460 | 0 |
| 1:1,000 | 0.270 | 0 |
| 1:10,000 | 0.015 | 0 |

The binding of various dilutions of the urine of an SLE patient and a healthy control were examined by ELISA. The lupus urine bound ECM, even when diluted 1:10,000.

TABLE 2

Urine Anti-ECM Response

| | Anti-ECM (O.D.) Mean + S.E. |
|---|---|
| Urine - SLE (n = 20) | 0.656 ± 0.1 |
| Urine MRL/lpr (n = 6) | 1.2 ± 0.05 |
| Urine - healthy controls (n = 10) | 0.009 ± 0.005 |
| Serum - SLE (n = 9) | 0.156 ± 0.08 |

The urine of SLE patients, healthy controls and MRL/lpr mice, was diluted 1:4, the serum of SLE patients was diluted 1:100, and their response with ECM was tested by ELISA. The urine of lupus patients and lupus mice was found to react with ECM.

TABLE 3

Correlation of Urinary Anti-ECM Response and Disease Activity

| | Anti-ECM (O.D.) | |
|---|---|---|
| | Before Treatment | After Treatment |
| Patient 1 | 1.8 | 0.01 |
| Patient 2 | 0.62 | 0.231 |
| Patient 3 | 0.580 | 0.272 |

The anti-ECM response in the urine of three SLE patients was tested when the disease was active and after response to treatment. The level of the anti-ECM antibodies was found to correlate with disease activity.

EXAMPLE 4

Urine and serum samples were obtained from 12 healthy volunteers and 22 SLE patients at the time of their visits for a check-up in the clinic. The results of the tests carried out are set forth below in Table 4. Urine and serum were aliquoted and frozen at −20° C. until use.

TABLE 4

Levels of Anti-ECM Antibodies in Urine from Subgroups of Lupus Patients and Mice[a]

|  | No. | Activity Index[b] | Albuminuria (gr/d) | Anti-ECM urinary, (O.D) |
|---|---|---|---|---|
| Active, Nephritis | 11 | 10.8 ± 1.27 | 2.3 ± 0.74 | 0.95 ± 0.12* |
| Active, No Nephritis | 5 | 8.6 ± 0.63 | ND[c] | 0.48 ± 0.08* |
| Not active | 6 | 2.2 ± 0.58 | 0.09 ± 0.09 | 0.14 ± 0.05 |
| Healthy volunteers | 12 | NT[d] | ND | 0.015 ± 0.007* |
| MRL/lpr/lpr mice | 5 | NT | NT | 1.15 ± 0.05** |
| Non lupus mice[e] | 5 | NT | NT | 0.03 ± 0.009 |

[a]Data are mean ± SE
[b]As defined by Lockshin et al. [6]
[c]ND = Not detected
[d]NT = Not tested
[e]C57BI6, BALB/C, CBA/N, (C57BI6 × BALB/C)F1 and MRL +/+ mice.
*p < 0.005 as compared to patients with inactive disease
**p < 0.005 as compared to non lupus mice All SLE patients met the 1982 ARA criteria for classification of SLE [E. M. Tan, et al., "The 1982 Revised Criteria for the Classification of Systemic Lupus Erythematosus," *Arth. Rheum.*, Vol. 25, pp. 1271–1277 (1982)]. 11 of the 22 patients had active nephritis at the time of the study. In two of them nephritis was diagnosed by urinalysis, revealing proteinuria and RBC casts. In the 9 other patients, a kidney biopsy was also performed, showing diffuse proliferative glomerulonephritis in 5 patients; membranous nephritis in 2 patients; and mesangiocapillary glumerulonephritis and interstitial nephritis, each in 1 patient. 5 patients had clinical active lupus, manifested mainly by diffuse skin rash in 2 patients; and by polyarthritis, polymyositis and central nervous system involvement, each in 1 patient. In addition, 3 of the patients had fever due to disease activity. The disease was defined as active when there was a need to start or increase the dose of corticosteroids, according to the treating physician. The remaining 6 patients were in clinical remission for more than 6 months. In addition, a clinical activity index was used, as described by Lockshin, et al., "Lupus Pregnancy: Case-Control Prospective Study Demonstrating Absence of Lupus Exacerbation during or after Pregnancy," *Am. J. Med.*, Vol. 77, pp. 893–898 (1984).

MRL/lpr, MRL +/+ C57B16, BALB/C (C57B16xBALB/C)F1 and CBA/N mice were purchased from Jackson Laboratories, Bar Harbour, Me., U.S.A. Urine was collected into 500 μl Eppendorf tubes by applying gentle pressure on the lower abdomen.

The NZB/NZW F1 derived monoclonal anti-DNA antibody C72 was a kind gift from Prof. D. Eilat, Hadassah University Hospital, Jerusalem. The binding specificities of this anti-DNA IgG antibody have been previously described [D. Eilat and R. Fischel, "Recurrent Utilization of Genetic Elements in V Regions of Anti-Nucleic Acid Antibodies from Autoimmune Mice," *J. Immunol.*, Vol. 147, pp. 361–368 (1991)].

Bovine corneal endothelial cells, donated by Prof. I. Vlodavski, Hadassah University Hospital, Jerusalem, were grown in Petri dishes as described above in Example 1. When the cells reached confluence, they were removed by Trypsin EDTA (0.25% trypsin, 0.02% EDTA, Biological Industries, Beit Haemek, Israel), washed, counted and cultured in 96 microwell plates (Nunc, Kinastrup, Denmark) in a concentration of $10^4$ cells/well. Ten days after seeding, the cell layer was dissolved by exposure to 0.5% Triton x-100 (Sigma Chemical Company, St. Louis, Mo., U.S.A.) in phosphate buffered saline (PBS) for 10 minutes at 22° C. Under these conditions, the ECM was left firmly attached to the wells.

The ECM-coated wells were incubated for 60 minutes with a blocking solution, composed of 10% fetal calf serum (Biological Industries) and 2% bovine serum albumin (Sigma). Prior to testing, urine was diluted 1:4 and serum was diluted to achieve an IgG level which is similar to that of the urinary samples. After washing the plates, serum or urine samples, diluted as mentioned above in PBS with 0.05% Tween 20 (PBS-Tween), were added and incubated for 90 minutes at room temperature. The plates were then washed with PBS-Tween and goat anti-human immunoglobulins peroxidase conjugate or goat anti-mouse IgG+IgM peroxidase conjugate 1:5000 (Jackson Immunoresearch Laboratories, West Grove, Pa., U.S.A.) were added to the wells and incubated for 45 minutes. The unbound conjugate was then removed by washing the plates and the substrate OPD (Sigma) was added. After 10 minutes, the reaction was stopped by the addition of 6N sulfuric acid and the optical density was measured photometrically at 492 mm. Uncoated, similarly blocked wells served as control for non-specific binding.

Serum and urine IgG from each patient were measured by ELISA. Polystyrene 96 well plates (Corning, N. Y., U.S.A.) were coated with 50 μl/well of AffiniPure goat anti-human IgG+IgM (Jackson Immunoresearch Laboratories) diluted 1:1000 in carbonate coating buffer (pH 9.6) at 4° C. overnight. Wells were washed 3 times with PBS-Tween 20 (0.05%) and blocked with 300 μl/well of 1% BSA in PBS for 30 minutes at room temperature. Wells were washed 3 times after blocking, and 50 μl/well of the appropriately diluted urine or serum were added to the wells. Known concentrations of human IgG (Gammonativ, Kabi, Pharmacia) were also placed in wells, to serve as a standard. Samples were incubated at room temperature for 1 hour and washed 6 times with PBS-Tween. Following washing, goat anti-human IgG+IgM peroxidase (Jackson Immunoresearch Laboratories) diluted 1:5000 in PBS was added at 50 μl/well and incubated at room temperature for 1 hour. Wells were washed 9 times in PBS-Tween and reaction was developed by the addition of 100 μl/well of O-Phenylenediamine 10 mg/30 ml in citrate buffer (pH 5.0) with 6 μl of 30% $H_2O_2$. The color reaction was stopped after 20 minutes by the addition of $H_2SO_4$ diluted 1:9.

Polystyrene 96 well plates (Nunc) were coated with 50 μl/well of 10 μg/ml Laminin (Sigma) in carbonate coating buffer (pH 9.6), 10 μg/ml DNA (Sigma) in PBS (pH 7.4) or 1:100 dilution of Matrigel (basement membrane matrigel, Collaborative Research Inc., Bradford, Massachusetts, U.S.A.) in BBS (borate buffered saline, pH 8.8). Matrigel is a commercial preparation of matrix produced by the EHS epithelial tumor that contains laminin as its major component [H.K. Kleinman, et al., "Basement Membrane Complexes with Biological Activity," *Biochemistry*, Vol. 25, pp. 312–318 (1986)]. Wells were coated and stored at 4° C. overnight. The wells were then washed 3 times with PBS- Tween 20 (0.05%) and blocked with 300 µl/well of 1% BSA in PBS for 30 minutes at room temperature. Before and during blocking, urine or C72 were mixed with different concentrations of inhibiting antigens and incubated 30 minutes at room temperature and 30 minutes at 4° C. Wells were washed 3 times after blocking, and 50 µl/well of the urine or C72 supernatant, with or without the inhibiting antigen, were added and incubated 90 minutes at room temperature. The wells were then washed 6 times and 50 µl/well of a second antibody anti-mouse IgG, conjugated to alkaline phosphatase (Sigma) 1:1000 or anti-human IgG+IgM conjugated to horseradish peroxidase (Jackson) 1:5000 were added and incubated 90 minutes at room temperature. The wells were washed 9 times, and the appropriate substrate solution was added at 100 µl/well. Results were read at 405 nm for alkaline phosphatase and 492 nm for HRP.

Antibody binding to DNA was also measured by using the Millipore (Bedford, Mass., U.S.A.) filter assay [B. Ginsberg and A. Keiser, "A Millipore Filter Assay for Antibodies to Native DNA in Sera of Patients with SLE," *Arthrits. Rheum.*, Vol. 16, pp. 199–207 (1973)]. Sera and urine were diluted in 0.2M borate-saline buffer, pH 8.0. 10 microliters of $^3$H-labelled DNA (6000 counts per minute) was added to 100 µl antibody. The mixture was incubated at 37° C. for 30 minutes and for an additional 60 minutes at 4° C. The mixture was filtered under reduced pressure, using 0.45 µm nitrocellulose filters (Millipore). The filters were washed twice with 3 ml aliquots of BBS and placed separately in plastic vials. The filters were dried at room temperature for at least 16 hours and read with toluene-based scintillation fluid in a beta scintillation counter. Results are expressed as the mean of duplicate samples. The samples differed from mean value by less than 8% of the mean.

Urine from an active lupus patient was centrifuged and the supernatant was passed through a protein A sepharose column (Sigma). The column was extensively washed with PBS and the immunoglobulins eluted with 0.1M citric acid. Immediately after elution, the immunoglobulins were neutralized with a 2M Tris solution (pH 11) and the O.D. read at 280 nm for calculation of immunoglobulin concentration. Following quantitation, the immunoglobulins were concentrated on Collodion bags (Sartorius AG, Gottingen, Germany), dialyzed against PBS for 3 days, and stored at 4° C. with 0.2% azide until use. IgG was quantitated by radial immunodiffusion, using NOR-Partigen IgG-MC plates (Behringwerke AG, Marburg, Germany).

MATRIGEL and laminin were run in 8% SDS gels, as described by Laemmli [U. K. Laemmli, "Cleavage of Structural Proteins during the Assembly of the Head of Bacteriophage T4, " *Nature*, Vol. 227, p. 680 (1970)], for 2.5 hours at 100 v. The proteins were transferred onto polyvinylidene difluoride (PVDF) membranes at 100v for 1.5 hours in a methanol-free Tris-glycine transfer buffer with the addition of 0.01% SDS. The membranes were blocked overnight at 4° C. with 10% goat serum in PBS, washed and reacted with 10 µg/ml IgG from the urine of a lupus patient or an equal amount of polyclonal human IgG (Gammonativ, Kabi, Pharmacia) diluted in 1% goat serum in PBS for 1 hour at room temperature. Membranes were washed again and incubated for another 1 hour with goat anti-human immunoglobulins alkaline phosphatase (Jackson), diluted 1:5000 in 1% goat serum in PBS. The membranes were washed again and the reaction was developed by incubation with 5-bromo-4-chloro-3-indolyl phosphate (BCIP) with nitro blue tetrazolium (NBT). Molecular weight markers were detected by staining with Coomassie protein stain.

Results

Urinary samples from 22 lupus patients, 12 healthy volunteers, 5 four-month-old MRL/lpr mice, MRL+/+ mice, and four strains of control non-lupus mice, were examined for the presence of anti-ECM antibodies by ELISA. As shown in Table 4 above, the urine of most of the lupus patients, as well as the urine of the lupus mice, contained high levels of anti-ECM antibodies (mean OD±SE: 0.65±0.11 and 1.15±0.05, respectively), whereas very low levels were found in the urine obtained from the healthy volunteers (OD 0.015±0.007), or the 5 strains of non-lupus mice (OD 0.03±0.009, not shown).

Immunoglobulin isolated from the urine of an SLE patient on a protein A column was shown to react with 200 kDa, 97 kDa and 116.7 kDa components of the MATRIGEL, as well as the 200 kDa chain of laminin. The 200 kDa correlates with the B1 and B2 chains of laminin. The lower molecular weight bands of MATRIGEL have not been identified and may be degradation products of higher molecular weight components. Similar concentration of polyclonal human immunoglobulins did not bind to either MATRIGEL or laminin.

When the patients were divided into patients with clinically active disease (16 patients, with a mean activity index of 10.2) and those with non-active disease (5 patients, with a mean activity index of 2.2), as described above, the active group had significantly higher levels of anti-ECM antibodies (OD 0.8±0.13) than the non-active (OD 0.14±0.05). Among the patients with active disease, the 11 patients who had clinical nephritis (mean albuminuria of 2.3 g/dl, casts, etc.) had the highest levels of anti-ECM antibodies (OD 0.95±0.12). Interestingly, the 5 patients who had active lupus with no clinical signs of nephritis, also had increased levels of these antibodies in their urine (0.48±0.08). Activity index of patients with nephritis was 10.8, while patients who had nephritis without clinical signs had an activity index of 8.6. Urine samples from patients with proteinuria due to amyloidosis and toxemia of pregnancy, as well as human immunoglobulins diluted in PBS-Tween in concentration between 0.1–10 mg/ml did not bind to ECM (not shown).

To test the difference in anti-ECM antibody levels between the serum and the urine, the antibodies in urine were compared to their level in serum that was diluted to a similar IgG concentration, and the results are correlated in Table 5 below. As shown in Table 5, anti-ECM antibodies were found mainly in the urine of lupus patients with a much lower concentration in the serum. No increase in ECM binding was observed in urine from healthy donors, even after addition of polyclonal human immunoglobulins (Gammonativ, Kabi, Pharmacia) in a concentration of 10 µg/ml.

TABLE 5

| | | Anti ECM* | |
|---|---|---|---|
| | Sample IgG | O.D. 492 nm | |
| Sample | concentration** | Urine | Serum |

Serum and Urine Levels of Anti-ECM Antibodies in Paired Samples

| Control*** | 10 | 0.02 | — |
| SLE pt. 1 | 5 | 0.24 | 0 |
| SLE pt. 2 | 2 | 0.23 | 0.05 |
| SLE pt. 3 | 62 | 0.93 | 0.25 |
| MRL/lpr mouse | 10 | 1.29 | 0 |

*Urine was diluted 1:4 and serum was brought to the same IgG concentration
**IgG measured by ELISA
***Immunoglobulin G (Kabi, Pharmacia) in urine from a healthy volunteer The results shown in Table 5 suggest that patients with active lupus have higher levels of urinary anti-ECM antibodies. To find whether the level of these antibodies correlates with disease activity, anti-ECM antibody levels were tested in 5 patients during active glomerulonephritis and a few weeks later when they improved after an increase in the corticosteroid dose, and the results are set forth below in Table 6. As can be seen in Table 6, the anti-ECM level decreased to very low levels, parallel to the decrease in disease activity. In one patient, the anti-ECM level was followed for 18 months. As can be seen in Table 6, the level of these antibodies correlated with disease activity. Moreover, the increase in the level of these antibodies preceded, by one week, a severe relapse of nephritis with nephrotic syndrome. Neither the degree of proteinuria, nor the level of anti-DNA antibodies or C3, were found to correlate better with disease activity in this patient than the urinary anti-ECM levels (data not shown).

TABLE 6

Correlation between Level of Anti-ECM Antibodies and Disease Activity

| | Disease Activity | | | | | |
|---|---|---|---|---|---|---|
| | Clinical Relapse | | | Clinical Remission | | |
| Patient | Activity index** | Album-inuria (gr/d) | Anti-ECM (O.D.) | Activity index | Album-inuria (gr/d) | Anti-ECM (O.D.) |
| 1. | 13 | 1.7 | 1.65 | 2 | 1.5 | ND*** |
| 2. | 8 | 1.4 | 0.96 | 1 | ND | ND |
| 3. | 7 | 0.9 | 0.7 | 3 | 0.4 | ND |
| 4. | 10 | 0.7 | 0.6 | 2 | 1.2 | 0.07 |
| 5. | 9 | 1.0 | 0.5 | 3 | 0.7 | 0.1 |

*Defined by the decision to start or increase corticosteroid treatment.
**As defined by Lockshin et al. [6].
***ND- not detected.

Referring first to FIG. 1, anti-ECM antibodies were measured repeatedly for 18 months in urine samples from a lupus patient during remission of her disease and during clinical relapse. The last sample was taken 3 weeks before clinical exacerbation of severe nephritis. The results are illustrated in said Figure.

Figure 2A:
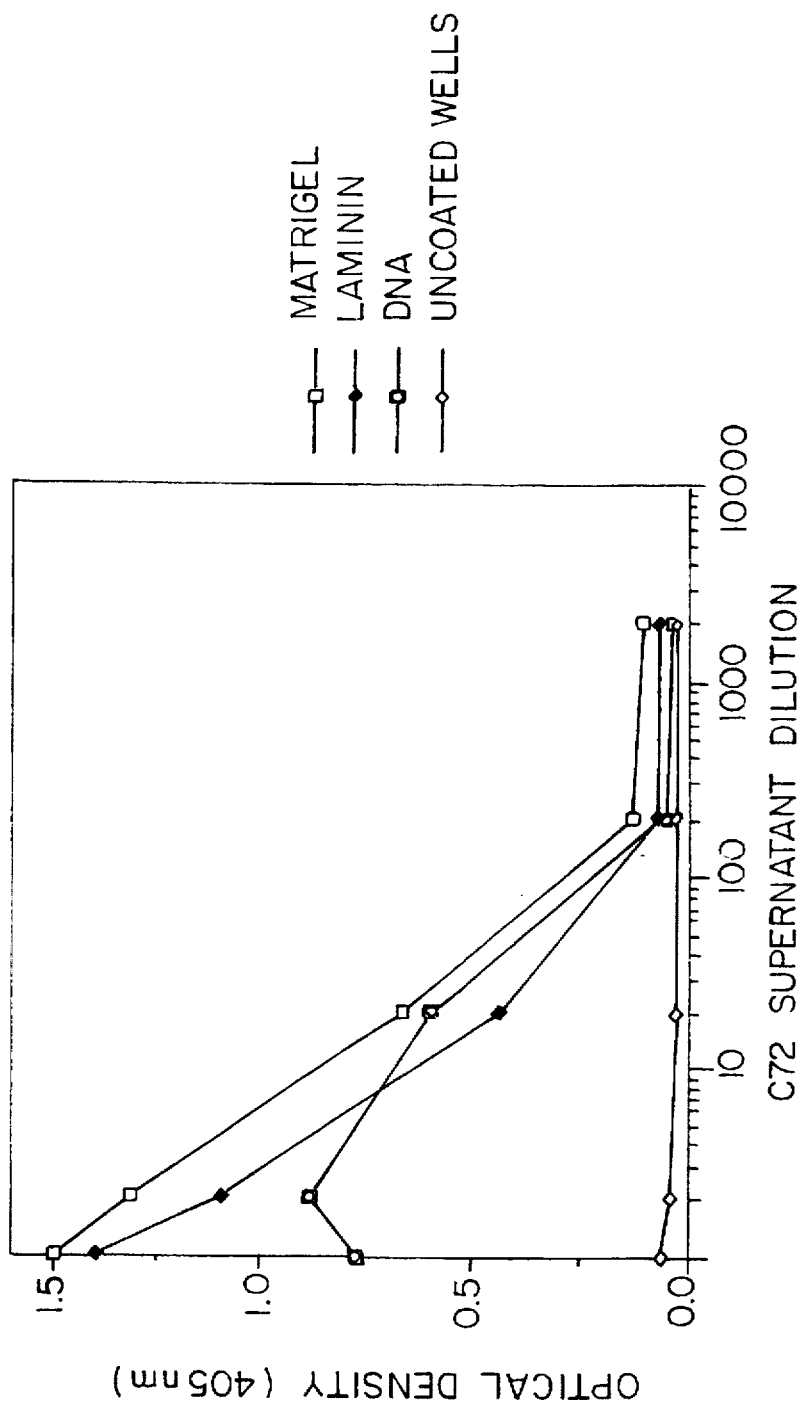
FIGS. 2A and 2B are graphic illustrations of the binding of monoclonal anti-DNA C72 antibody and urine from an SLE patient to several antigens.
Figure 2B:
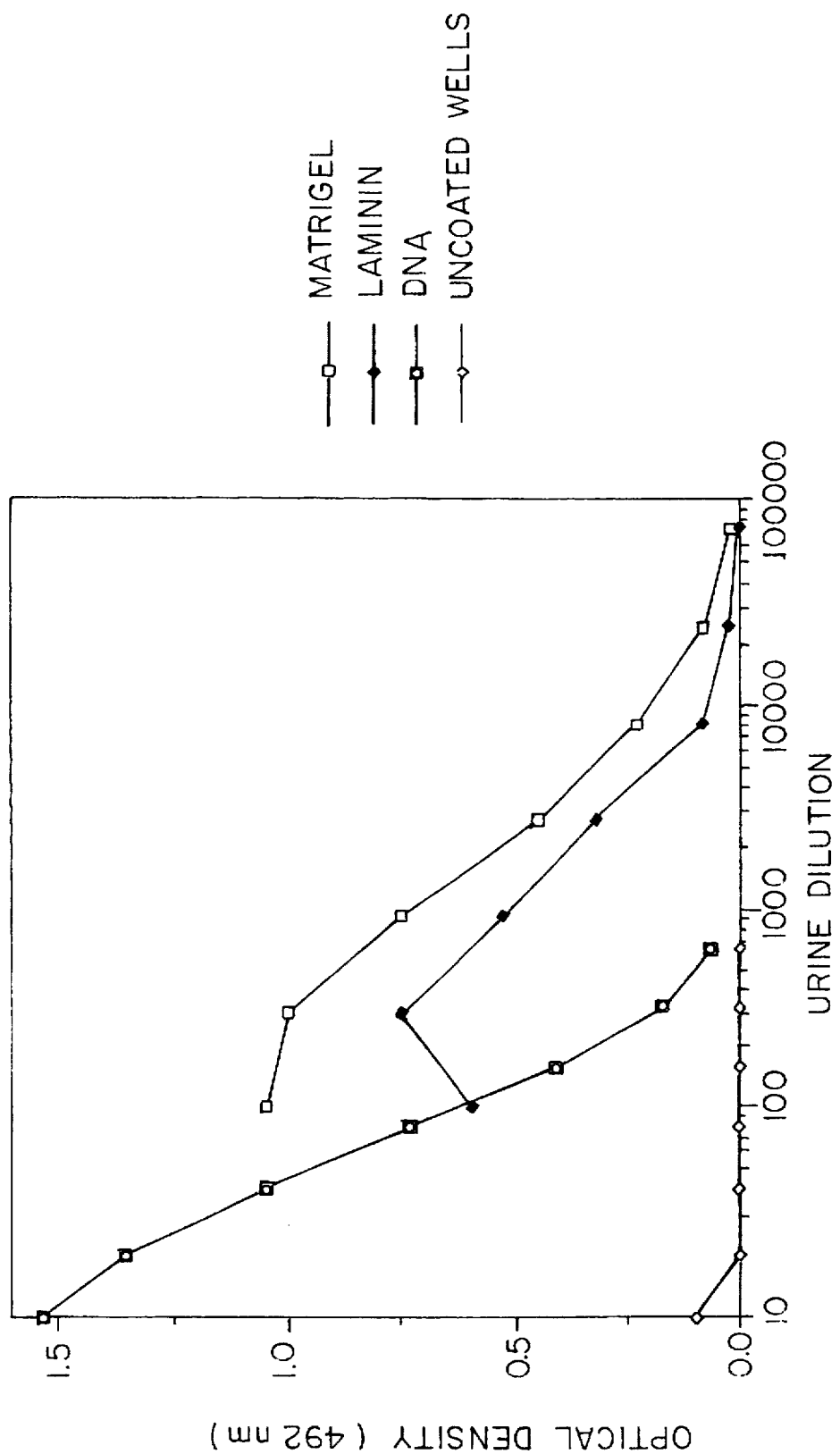

Referring now to FIGS. 2A and 2B, binding was measured by ELISA on wells coated with the tested antigens, reacted with C72 supernatant (FIG. 2A) or urine (FIG. 2B) from an SLE patient and detected by an anti-mouse alkaline phosphatase conjugate or anti-human horseradish peroxidase.

A murine monoclonal anti-DNA antibody C72 was shown to react to MATRIGEL and laminin in a similar fashion to its reactivity to DNA (FIG. 2A). This pattern of reactivity resembled antibodies found in the urine of lupus patients that reacted with all three antigens, but were more reactive to MATRIGEL and laminin than to DNA (FIG. 2B). This suggests the possibility that laminin, which is a major ingredient in MATRIGEL [H. K. Kleinman, et al., "Basement Membrane Complexes with Biological Activity," Biochemistry, Vol. 25, pp. 312-318 (1986)] is the target antigen of antibodies found in lupus patients, as well as of the anti-DNA antibodies in the murine lupus model.

Figure 3A:
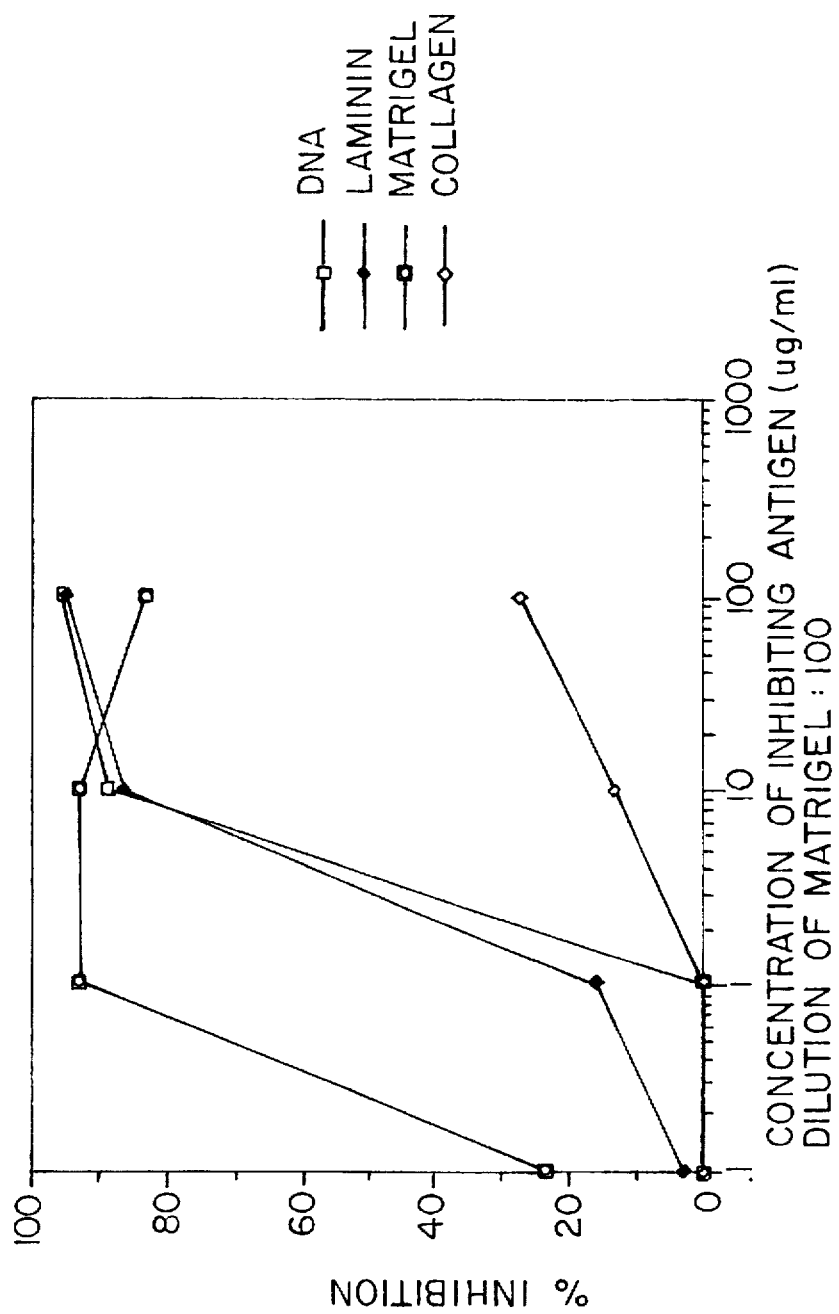

Referring now to FIGS. 3A and 3B, binding was measured by ELISA. Inhibition was performed by preincubation of the C72 supernatant (FIG. 3A) or urine (FIG. 3B) from an SLE patient with different concentrations of the inhibiting antigen. Percent inhibition was calculated as the percentage of the optical density of the antibody preincubated with PBS only.

As can be seen from said figures, MATRIGEL and laminin could inhibit the reactivities of both the monoclonal and the polyclonal urinary antibodies; DNA could also inhibit the reactivity to all antigens but that which occurred at higher concentrations of the inhibiting antigen (FIGS. 3A. 3B). The specificity of the inhibition was demonstrated by the complete inability of collagen, another very common ingredient of basement membranes, to inhibit any of the reactivities of lupus urinary antibodies (FIG. 3B) or the monoclonal C72 antibody (FIG. 3A).

It will be evident to those skilled in the art that the invention is not limited to the details of the foregoing illustrative examples, and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A binding assay method for determining the level of antibodies found in the urine of lupus disease patients, comprising:
   a) incubating a urine sample from a suspected lupus disease patient, said sample in contact with a solid carrier having extracellular matrix or a lupus antibody-binding laminin component thereof fixed on at least a portion of its surface;
   b) washing said carrier to remove residual sample;
   c) incubating the solid carrier with anti-human/mouse IgG peroxidase or alkaline phosphatase conjugate;
   d) incubating said solid carrier in contact with a suitable enzyme substrate which undergoes color change in the presence of bound conjugate;
   e) measuring the intensity of resultant color; and
   f) comparing the intensity measured in e) to an intensity measured in a sample from at least one source selected from the group consisting of a lupus disease patient and non-lupus diseased control as a measure of the level of said antibodies found in the urine of lupus disease patients.

2. A binding assay method according to claim 1, wherein said urine is incubated in contact with a solid carrier having laminin fixed on at least a portion of its surface.

3. A binding assay method according to claim 2, wherein said laminin has a molecular weight of about 200 kDa.

4. A binding assay method for determining the progression of lupus disease in a patient, comprising:
   a) incubating a urine sample from a lupus disease patient, said sample in contact with a solid carrier having extracellular matrix or a lupus antibody-binding laminin component thereof fixed on at lease a portion of its surface;
   b) washing said carrier to remove residual sample;
   c) incubating the solid carrier with anti-human/mouse IgG peroxidase or alkaline phosphatase conjugate;
   d) incubating said solid carrier in contact with a suitable enzyme substrate which undergoes color change in the presence of bound conjugate;
   e) measuring the intensity of resultant color;
   f) repeating steps a) to e) with fresh urine samples obtained from said patient, after a predetermined number of days; and
   g) comparing the intensity obtained in e) with the intensity obtained in f), wherein a difference in the intensity obtained in f) as compared to the intensity obtained in e) indicates a corresponding difference in the progression of lupus disease in said patient.

5. A binding assay method according to claim 4, wherein said urine is incubated in contact with a solid carrier having laminin fixed on at least a portion of its surface.

6. A binding assay method according to claim 5, wherein said laminin has a molecular weight of about 200 kDa.

7. A binding assay method for predicting an active phase of lupus disease in a patient with disposition to said disease, comprising:

a) incubating a urine sample from a lupus disease patient, said sample in contact with a solid sample in contact with a solid carrier having extracellular matrix or a lupus antibody-binding laminin component thereof fixed on at least a portion of its surface;

b) washing said carrier to remove residual sample;

c) incubating the solid carrier with anti-human/mouse IgG peroxidase or alkaline phosphatase conjugate;

d) incubating said solid carrier in contact with a suitable enzyme substrate which undergoes color change in the presence of bound conjugate;

e) measuring the intensity of resultant color; and f) comparing the intensity measured in e) to an intensity measured in a sample from at least one source selected from the group consisting of a lupus disease patient and a non-lupus diseased control as an indication of the likelihood of the occurrence of an active phase of lupus disease in said patient.

8. A binding assay method according to claim 7, wherein said urine is incubated in contact with a solid carrier having laminin fixed on at least a portion of its surface.

9. A binding assay method according to claim 8, wherein said laminin has a molecular weight of about 200 kDa.

* * * * *